United States Patent
Koga

(10) Patent No.: US 12,330,139 B2
(45) Date of Patent: Jun. 17, 2025

(54) METHOD FOR EXTRACTING LOW-MOLECULAR-WEIGHT SUBSTANCE EXISTING IN BIOLOGICAL SAMPLE

(71) Applicant: TAS PROJECT CO. LTD., Fukuoka (JP)

(72) Inventor: Yoshiyuki Koga, Fukuoka (JP)

(73) Assignee: TAS PROJECT CO. LTD, Fukuoka (JP)

( * ) Notice: Subject to any disclaimer, the term of this patent is extended or adjusted under 35 U.S.C. 154(b) by 591 days.

(21) Appl. No.: 17/789,445

(22) PCT Filed: Dec. 21, 2020

(86) PCT No.: PCT/JP2020/047735
§ 371 (c)(1),
(2) Date: Jun. 27, 2022

(87) PCT Pub. No.: WO2021/132178
PCT Pub. Date: Jul. 1, 2021

(65) Prior Publication Data
US 2023/0029620 A1 Feb. 2, 2023

(30) Foreign Application Priority Data
Dec. 26, 2019 (JP) .................. 2019-236585

(51) Int. Cl.
*B01J 20/283* (2006.01)
*B01D 15/08* (2006.01)
(Continued)

(52) U.S. Cl.
CPC ............ *B01J 20/283* (2013.01); *B01D 15/08* (2013.01); *B01J 20/20* (2013.01); *B01J 20/34* (2013.01); *G01N 30/06* (2013.01); *G01N 33/48* (2013.01)

(58) Field of Classification Search
CPC .......... B01D 15/00; B01D 15/08; B01J 20/20; B01J 20/28; B01J 20/281; B01J 20/282;
(Continued)

(56) References Cited

U.S. PATENT DOCUMENTS

| 4,584,399 A | 4/1986 | Portal et al. |
| 2008/0025907 A1 | 1/2008 | Tennison et al. |

(Continued)

FOREIGN PATENT DOCUMENTS

| JP | S59-176215 A | 10/1984 |
| JP | S61-148147 A | 7/1986 |

(Continued)

OTHER PUBLICATIONS

May 6, 2023 Office Action issued in Chinese Patent Application No. 202080089803.2.

(Continued)

*Primary Examiner* — Brian A McCaig
(74) *Attorney, Agent, or Firm* — Oliff PLC

(57) ABSTRACT

A method for extracting a low-molecular-weight substance existing in a biological sample, including: 1) an adsorption step of adsorbing the substance on porous carbon by mixing the biological sample with the porous carbon having mesopores of 3.5 nm to 150 nm and micropores of a larger size as a hierarchical structure, and recovering the porous carbon from the obtained mixture, or by bringing the biological sample into contact with a filtration filter on which the porous carbon is disposed or supported; and 2) a releasing step of releasing the low-molecular-weight substance from the porous carbon by mixing the porous carbon obtained after the adsorption step with an aqueous solution containing 0.1 mass % to 1 mass % of spherical silica having an average particle diameter of 10 nm to 100 nm and containing 10% to (Continued)

12% of acetonitrile, or by causing the filtration filter to contact and pass through the aqueous solution.

10 Claims, 3 Drawing Sheets

(51) Int. Cl.
    *B01J 20/20*     (2006.01)
    *B01J 20/34*     (2006.01)
    *G01N 30/06*     (2006.01)
    *G01N 33/48*     (2006.01)

(58) Field of Classification Search
    CPC ........ B01J 20/283; B01J 20/288; B01J 20/34; G01N 1/10; G01N 30/06; G01N 30/52; G01N 33/48; G01N 2030/525
    See application file for complete search history.

(56) References Cited

U.S. PATENT DOCUMENTS

| | | |
|---|---|---|
| 2008/0213557 A1 | 9/2008 | Vinu et al. |
| 2009/0136816 A1 | 5/2009 | Kang et al. |
| 2011/0082024 A1 | 4/2011 | Liu et al. |
| 2011/0237691 A1 | 9/2011 | Tennison et al. |
| 2012/0058568 A1 | 3/2012 | Sasaki et al. |
| 2012/0178618 A1 | 7/2012 | Vinu et al. |
| 2017/0121186 A1* | 5/2017 | Fichtner ............ B01D 39/2058 |

FOREIGN PATENT DOCUMENTS

| | | |
|---|---|---|
| JP | 2006-206397 A | 8/2006 |
| JP | 2007-205927 A | 8/2007 |
| JP | 2008-120633 A | 5/2008 |
| JP | 2009-132607 A | 6/2009 |
| JP | 2011-168484 A | 9/2011 |
| JP | 2011-525468 A | 9/2011 |
| JP | 2013-003065 A | 1/2013 |
| WO | 2010/100914 A1 | 9/2010 |
| WO | 2011/114470 A1 | 9/2011 |

OTHER PUBLICATIONS

Jun. 19, 2024 Office Action issued in Japanese Patent Application No. 2021-567453.
Mar. 9, 2021 International Search Report issued in International Patent Application No. PCT/JP2020/047735.
Mar. 9, 2021 Written Opinion of the International Searching Authority issued in International Patent Application No. PCT/JP2020/047735.

* cited by examiner

METHOD FOR EXTRACTING LOW-MOLECULAR-WEIGHT SUBSTANCE EXISTING IN BIOLOGICAL SAMPLE

TECHNICAL FIELD

The present invention relates to a method for extracting a low-molecular-weight substance existing in a biological sample.

BACKGROUND ART

As a method for adsorbing and removing a low-molecular-weight substance existing in a biological sample, a method using activated carbon is known.

For example, JP S59-176215 A (Patent Document 1) describes a method for removing a low-molecular-weight portion from an IgG fraction after dialysis by using activated carbon, and WO 2011/114470 A1 (Patent Document 2) describes a method for efficiently separating and removing impurities from a hyaluronic acids-containing liquid by using activated carbon.

In addition, JP S61-148147 A (Patent Document 3) describes a method for purifying L-phenylalanine including adsorbing L-phenylalanine on activated carbon and then eluting L-phenylalanine from the activated carbon.

Although adsorption and elution of L-phenylalanine are performed by using activated carbon in Patent Document 3, it is generally not easy to efficiently release and recover the low-molecular-weight substance adsorbed on the activated carbon.

PRIOR ART DOCUMENTS

Patent Documents

Patent Document 1: JP S59-176215 A
Patent Document 2: International Publication Pamphlet WO 2011/114470
Patent Document 3: JP S61-148147 A

SUMMARY OF THE INVENTION

Problems to be Solved by the Invention

In order to solve a problem for the present invention, an object of the present invention is to provide a method capable of easily extracting a low-molecular-weight substance existing in a biological sample.

Means for Solving the Problems

As a result of intensive studies to solve the above problem, the present inventor has found that porous carbon having mesopores of 3.5 nm to 150 nm and micropores of a larger size as a hierarchical structure can efficiently adsorb a low-molecular-weight substance existing in a biological sample, and that by bringing porous carbon that has adsorbed the low-molecular-weight substance into contact with an aqueous solution containing 0.1 mass % to 1 mass % of spherical silica having an average particle diameter of 10 nm to 100 nm and containing 10% to 12% of acetonitrile, the adsorbed low-molecular-weight substance can be easily released and thus the low-molecular-weight substance can be recovered at a high recovery rate, thereby completing the present invention.

That is, the present invention relates to:

[1] A method for extracting a low-molecular-weight substance existing in a biological sample from the sample, the method including:
1) an adsorption step of adsorbing the low-molecular-weight substance on porous carbon by mixing the biological sample with the porous carbon having mesopores of 3.5 nm to 150 nm and micropores of a larger size as a hierarchical structure, and then recovering the porous carbon from the obtained mixture, or by bringing the biological sample into contact with a filtration filter on which the porous carbon having mesopores of 3.5 nm to 150 nm and micropores of a larger size as a hierarchical structure is disposed or supported; and
2) a releasing step of releasing the low-molecular-weight substance from the porous carbon by mixing the porous carbon having the low-molecular-weight substance adsorbed thereon, obtained after the adsorption step, with an aqueous solution containing 0.1 mass % to 1 mass % of spherical silica having an average particle diameter of 10 nm to 100 nm and containing 10% to 12% of acetonitrile, or by causing the filtration filter obtained after the adsorption step to contact and pass through the aqueous solution;

[2] the method according to [1] above, further including a regeneration step of regenerating the porous carbon after the releasing step for use in the adsorption step again;

[3] the method according to [1] or [2] above, further including a pretreatment step of the biological sample before the adsorption step;

[4] the method according to any one of [1] to [3] above, wherein the spherical silica is a surface-treated spherical silica; and

[5] the method according to [4] above, wherein the surface-treated spherical silica has been subjected to a treatment of substituting a silanol group on the surface of the spherical silica with a phenyl group, a vinyl group, or a methacryloyloxy group.

Effects of the Invention

According to the present invention, it is possible to provide a method capable of easily extracting a low-molecular-weight substance existing in a biological sample.

In addition, the method of the present invention can continuously extract a low-molecular-weight substance from a large number of biological samples by adding a step of regenerating porous carbon after a releasing step.

Furthermore, the method of the present invention makes it possible to extract a low-molecular-weight substance from various different biological samples such as serum by adding a pretreatment step of the biological sample before an adsorption step.

BRIEF DESCRIPTION OF THE DRAWINGS

FIG. 3 shows HPLC charts obtained by HPLC analysis of four consecutive fractions (0.25 mL each) obtained by injecting an eluent (10% acetonitrile solution in which 0.1 mass % of spherical silica is suspended: 1 mL) into a cartridge having porous carbon that has absorbed 8-oxo-dG, in which

MODES FOR CARRYING OUT THE INVENTION

Figure 1:
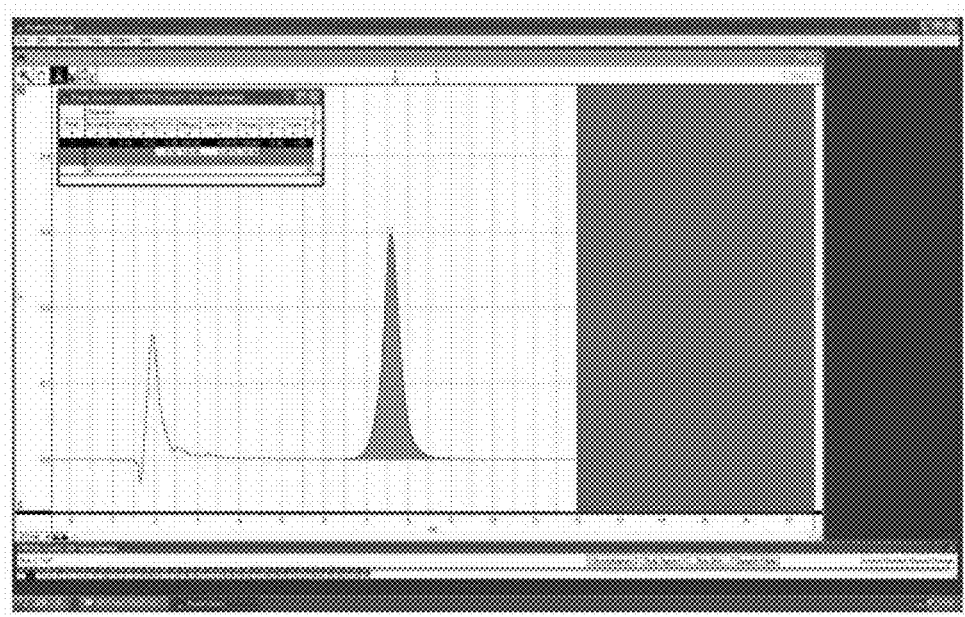
FIG. 1 is an HPLC chart obtained by HPLC analysis of a simulated biological sample (8-oxo-dG: 250 ng/mL) containing a standard 8-oxo-dG before filtration with a cartridge of a Millipore filter having porous carbon.

The present invention will be described in further detail.

A method for extracting a low-molecular-weight substance existing in a biological sample from the sample is characterized by including:

1) an adsorption step of adsorbing the low-molecular-weight substance on porous carbon by mixing the biological sample with the porous carbon having mesopores of 3.5 nm to 150 nm and micropores of a larger size as a hierarchical structure, and then recovering the porous carbon from the obtained mixture, or by bringing the biological sample into contact with a filtration filter on which the porous carbon having mesopores of 3.5 nm to 150 nm and micropores of a larger size as a hierarchical structure is disposed or supported; and
2) a releasing step of releasing the low-molecular-weight substance from the porous carbon by mixing the porous carbon having the low-molecular-weight substance adsorbed thereon, obtained after the adsorption step, with an aqueous solution containing 0.1 mass % to 1 mass % of spherical silica having an average particle diameter of 10 nm to 100 nm and containing 10% to 12% of acetonitrile, or by causing the filtration filter obtained after the adsorption step to contact and pass through the aqueous solution.

Examples of the biological sample that can be used in the present invention include urine, serum, an extract from tissues, and an extract from cells, and a biological sample in which no precipitate is present is preferable.

Examples of preferable biological samples include urine and serum, and urine is preferable.

Examples of the low-molecular-weight substance to be subjected to the present invention include nucleic acids or derivatives thereof (nucleotides, nucleosides and/or bases, etc.), peptides, amines, steroids, fatty acids, vitamins, and other low-molecular-weight compounds, and preferably include compounds having a molecular weight of 5000 or less.

Preferable examples of the low-molecular-weight substance include low-molecular-weight compounds such as nucleic acid derivatives such as dG (deoxyguanosine), 8-oxo-dG, and various mononucleosides, peptides, drugs (such as narcotic drugs and doping agents), amines, steroids, fatty acids, vitamins and creatinine, and nucleic acid derivatives such as dG (deoxyguanosine) and 8-oxo-dG are preferable.

As the porous carbon having mesopores of 3.5 nm to 150 nm and micropores of a larger size as a hierarchical structure that can be used in the present invention, pore-controlled mesoporous carbon obtained by controlling the size of the mesopores using a metal oxide having a specific size as a template, for example, MgO, is preferable.

The average particle diameter of the porous carbon that can be used in the present invention is, for example, 1 μm to 100 μm, preferably 1 μm to 10 μm.

Specific examples of the porous carbon that can be used in the present invention include CNovel (registered trademark) MJ(4)010 (designed mesopore diameter: 10 nm), MJ(4)030 (designed mesopore diameter: 30 nm), MJ(4)110 (designed mesopore diameter: 110 nm), and MJ(4)150 (designed mesopore diameter: 150 nm) available from Toyo Tanso Co., Ltd., and MJ(4)110 is preferable.

The filtration filter that can be used in the present invention is not particularly limited as long as it includes a filtration membrane having such a pore size that the porous carbon does not leak, and examples thereof include Millipore filters, and specifically include DISMIC 13HP045AN (Teflon (registered trademark) (PTFE) filtration membrane (pore size 0.45 μm), membrane diameter: 13 mm) and DISMIC 03JP050AN (Teflon (registered trademark) (PTFE) filtration membrane (pore size 0.50 μm), membrane diameter: 3 mm) available from Advantec Toyo Kaisha, Ltd.

The spherical silica having an average particle diameter of 10 nm to 100 nm that can be used in the present invention is not particularly limited as long as it is spherical silica having an average particle diameter of 10 nm to 100 nm, but is preferably spherical silica having an average particle diameter of 10 nm to 50 nm or spherical silica having an average particle diameter of 10 nm to 30 nm.

In addition, the spherical silica is preferably subjected to surface treatment in order to increase affinity with a hydrophilic substance, and as specific surface treatment, substitution of a silanol group on the surface of the spherical silica with a phenyl group, a vinyl group, or a methacryloyloxy group is preferable, and in particular, substitution of a silanol group with a vinyl group is preferable.

Specific examples of the spherical silica that can be used in the present invention include ADMANANO YA010C (average particle diameter: 10 nm), ADMANANO YA010C-SV1 (average particle diameter: 10 nm, surface treatment: vinylated), ADMANANO YA030C (average particle diameter: 30 nm), and ADMANANO YC100C (average particle diameter: 100 nm) available from Admatechs Company Limited, and ADMANANO YA010C-SV1 (average particle diameter: 10 nm, surface treatment: vinylated) is preferable.

In the present specification, the average particle diameter is intended as a value of a particle diameter D50 (median diameter) of a particle size distribution (volume basis) obtained by a laser diffraction scattering method, and the spherical silica is indented as silica particles having a spherical coefficient of variation ($\sigma/D$ (%), $\sigma$: standard deviation of particle diameter, D: average particle diameter) of 20% or less, preferably 15% or less.

The adsorption step in the method of the present invention is characterized by adsorbing the low-molecular-weight substance on porous carbon by mixing the biological sample with the porous carbon having mesopores of 3.5 nm to 150 nm and micropores of a larger size as a hierarchical structure, and then recovering the porous carbon from the obtained mixture, or by bringing the biological sample into contact with a filtration filter on which the porous carbon having mesopores of 3.5 nm to 150 nm and micropores of a larger size as a hierarchical structure is disposed or supported.

The adsorption step that can be used in the method of the present invention is not particularly limited as long as it is a step of mixing a biological sample with porous carbon having mesopores of 3.5 nm to 150 nm and micropores of a larger size as a hierarchical structure, but it is preferable that the biological sample is gently mixed and sufficiently degassed with ultrasonic waves or the like so that air bubbles do not block the pores on the surface of the porous carbon.

In addition, the filtration filter on which porous carbon is disposed can be used in the form of a cartridge in which a gap between two filters is filled with porous carbon.

In the case of using the above cartridge, it is preferable that the inner surface of the cartridge and the surface of the porous carbon are covered with water molecules so that air bubbles are not mixed in.

Examples of the operation in the case of using the above cartridge include filtration by injecting the biological sample into a cartridge filled with porous carbon using a syringe.

At the time of injection, it is preferable to perform injection so that the pressure is as constant as possible.

Furthermore, examples of the filtration filter on which porous carbon is supported include a filtration filter on which porous carbon is fixed by a known method.

The releasing step in the method of the present invention is characterized by releasing the low-molecular-weight substance from the porous carbon by mixing the porous carbon having the low-molecular-weight substance adsorbed thereon, obtained after the adsorption step, with an aqueous solution containing 0.1 mass % to 1 mass % of spherical silica having an average particle diameter of 10 nm to 100 nm and containing 10% to 12% of acetonitrile, or by causing the filtration filter obtained after the adsorption step to contact and pass through the aqueous solution.

In the releasing step, the acetonitrile aqueous solution containing the spherical silica comes into contact with the porous carbon having the low-molecular-weight substance adsorbed thereon, thus a water-soluble substance trapped in the pores of the porous carbon is replaced by the spherical silica having affinity for the porous carbon, and as a result, the water-soluble substance is released into the solution.

When the acetonitrile aqueous solution containing the spherical silica is prepared, it is preferable to perform ultrasonic treatment for the purpose of homogenizing and degassing the solution.

In addition, in the case where the filtration filter obtained after the adsorption step is caused to contact and pass through the aqueous solution, it is preferable to inject the acetonitrile aqueous solution containing the spherical silica into the filtration filter using a syringe, and at that time, it is preferable to perform the injection at a pressure as constant as possible.

The method of the present invention also relates to an invention of a method further including a regeneration step of regenerating the porous carbon after the releasing step for use in the adsorption step again.

The regeneration step may include a washing step and a drying step.

Specific examples of the washing step include washing the porous carbon after the releasing step with 100% acetonitrile, then with 10% acetonitrile aqueous solution, and finally with ultrapure water.

In addition, examples of the drying step include heating and drying the porous carbon after the washing step, at a temperature of 120° C. to 180° C. for 1 to 8 hours.

By including the above regeneration step, a low-molecular-weight substance can be continuously extracted from a large number of biological samples by, for example, an automatic operation through the night.

In addition, the above-described continuous extraction method can be advantageously used not only as an extraction method but also as an analysis method.

The method of the present invention also relates to a method further including a pretreatment step of the biological sample before the adsorption step.

As the pretreatment step of the biological sample, a known pretreatment method can be used, and examples thereof include separation by a precolumn, centrifugation, dialysis membrane separation, denaturing precipitation, enzyme treatment, and the like.

The above pretreatment enables extraction of low-molecular-weight substances from various biological samples.

EXAMPLES

Test Example 1: Extraction of 8-Oxo-dG from Artificial Urine

<Preparation of Simulated Biological Sample Containing 8-oxo-dG>

A simulated biological sample was prepared by dissolving a standard 8-oxo-dG in artificial urine (JIS code T3214: 2011) so as to have a concentration of 250 ng/mL.

<Preparation of Cartridge of Millipore Filter Having Porous Carbon>

Porous carbon (functional activated carbon having CNovel (registered trademark) MJ(4)110 (designed mesopore diameter: 110 nm) in a three-dimensional structure at high density, particle diameter: about 5 μm or less, hydrophilic, manufactured by Toyo Tanso Co., Ltd.) was gently mixed in ultrapure water (without bubbling) so as to reach an amount of 1 mg/mL, an ultrasonic wave of 100 KHz was applied for 5 minutes to sufficiently degas so that air bubbles did not block the pores, and thus a porous carbon suspension liquid was prepared.

1 mL of the porous carbon suspension liquid prepared above was filtered through a Millipore filter (DISMIC 13HP045AN, Teflon (registered trademark) (PTFE) filtration membrane (pore size 0.45 μm), membrane diameter: 13 mm, manufactured by Advantec Toyo Kaisha, Ltd.) using a syringe to uniformly fill the front pores of the filtration membrane with porous carbon.

Next, a second Millipore filter (DISMIC 13HP045AN, Teflon (registered trademark) (PTFE) filtration membrane (pore size 0.45 μm), membrane diameter: 13 mm, manufactured by Advantec Toyo Kaisha, Ltd.) was connected to the above-described Millipore filter filled with the porous carbon, and 1 mL of ultrapure water was slowly passed therethrough to securely retain the porous carbon between the front and rear two filtration membranes. In consideration of preventing air bubbles from being mixed into the space of the cartridge formed by connecting two Millipore filters, the inner surface of the cartridge and the surface of carbon atoms of the porous carbon were covered with water molecules.

<Preparation of Eluent>

In 100% acetonitrile, 1 mass % of hydrophilic spherical silica (ADMANANO YA010C-SV1, average particle diameter 10 nm, surface treatment: vinylated, manufactured by Admatechs Company Limited) was mixed and floated (original eluent). For the purpose of homogenization and degassing of the solution, an ultrasonic wave of 100 KHz was applied, and the storage was performed at room temperature.

The original eluent was diluted 10 times with ultrapure water at the time of use to obtain an eluent (10% acetonitrile solution in which 0.1 mass % of spherical silica is floated).

<Filtration of Simulated Biological Sample (Filtration and Adsorption of 8-oxo-dG in Sample)>

1 mL of the simulated biological sample containing the standard 8-oxo-dG prepared above was filtered through the cartridge of a Millipore filter having porous carbon prepared above using a syringe at a pressure as constant as possible while setting 1 mL/min as a standard.

The sample was analyzed by HPLC before and after filtration.

Figure 2:
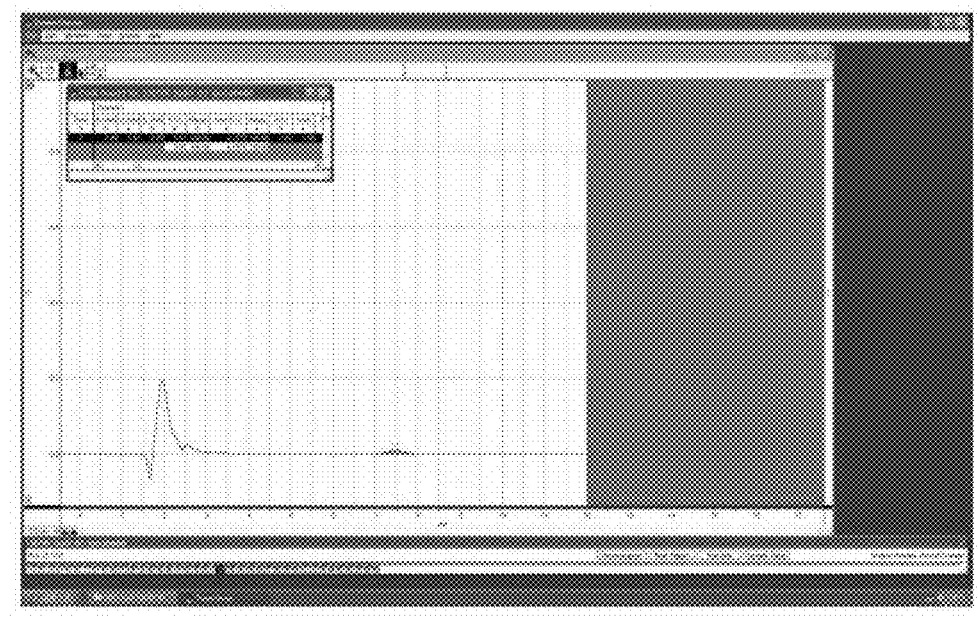
FIG. 2 is an HPLC chart obtained by HPLC analysis of a filtrate obtained after filtering a simulated biological sample containing a standard 8-oxo-dG with a cartridge of a Millipore filter having porous carbon.
Figure 3A:
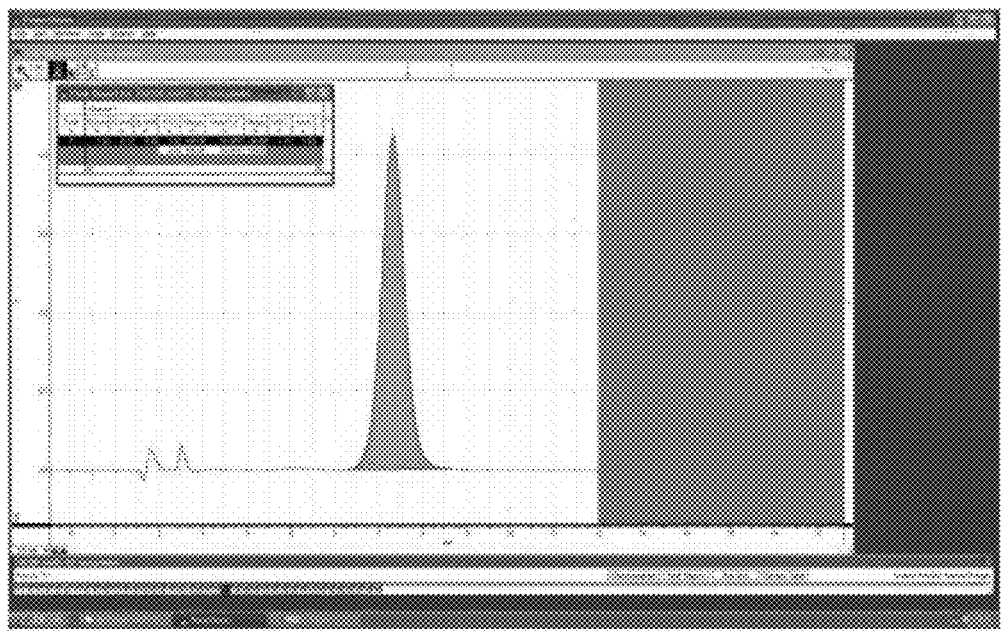
FIG. 3A shows an HPLC chart of a fraction of 0 mL to 0.25 mL.
Figure 3B:
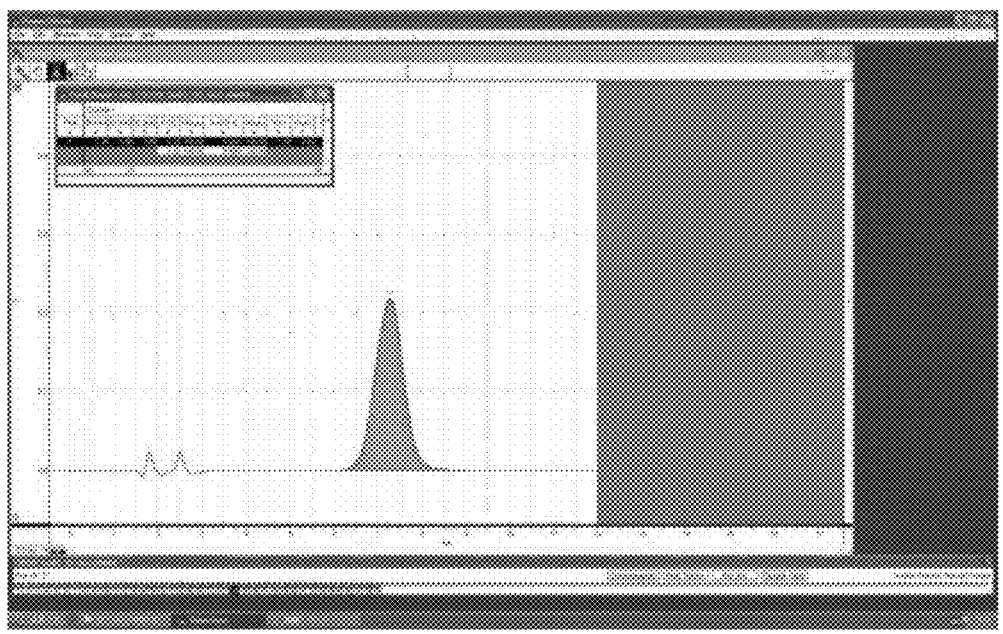
FIG. 3B shows an HPLC chart of a fraction of 0.25 mL to 0.5 mL.
Figure 3C:
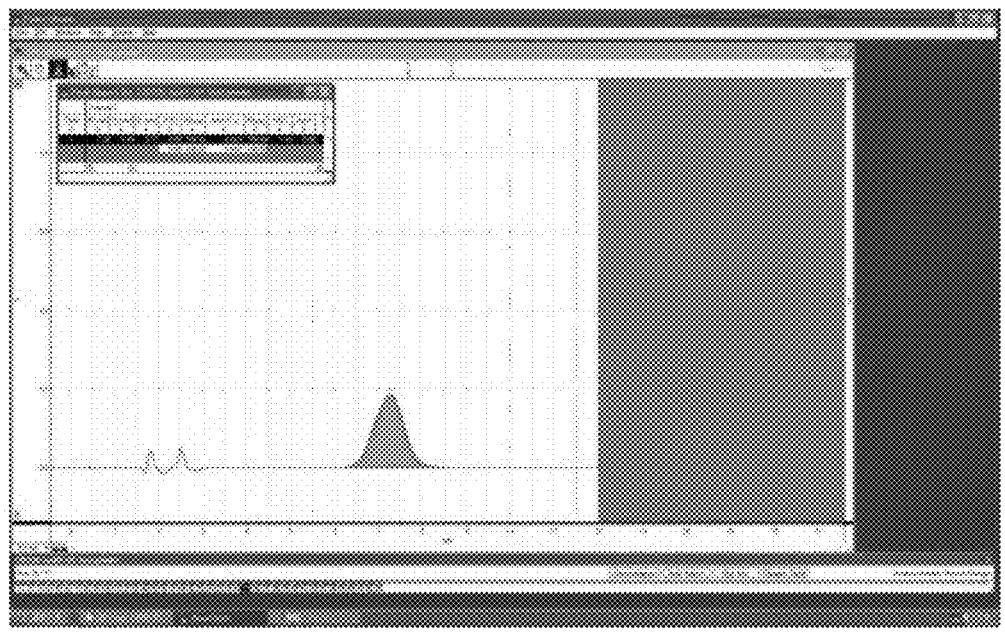
FIG. 3C shows an HPLC chart of a fraction of 0.5 mL to 0.75 mL.
Figure 3D:
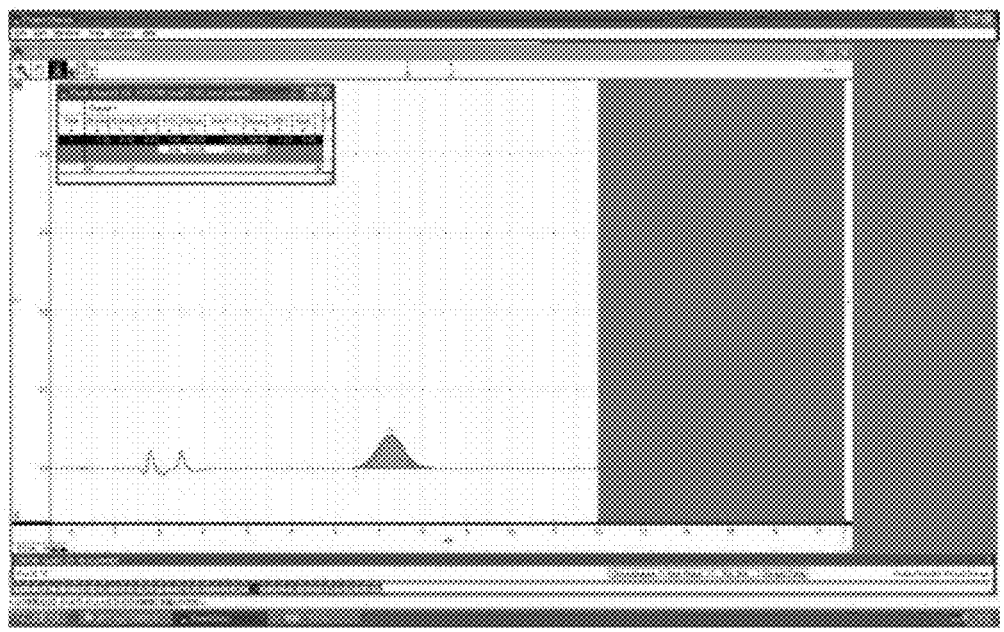
FIG. 3D shows an HPLC chart of a fraction of 0.75 mL to 1.0 mL.

The HPLC chart before filtration is shown in FIG. 1, and the HPLC chart after filtration is shown in FIG. 2.

Analysis conditions of HPLC are shown below.

HPLC Analysis Conditions

Instrument: HTEC-500 (manufactured by EICOM Corporation) (8-oxo-dG is electrochemically detected)

ODS column: CA-5ODS, column size: 2.1φ×150 mm (manufactured by EICOM Corporation)

Mobile phase: phosphate buffer solution (pH 6.5-6.8), methanol 2%, SDS 90 mg/L

As a result of calculation as a ratio % in the case where the peak area of the HPLC measurement value of the 8-oxo-dG standard solution (250 ng/mL) was set as 100, the amount of 8-oxo-dG adsorbed on the porous carbon was 98.2% of the amount of 8-oxo-dG contained in the simulated biological sample.

<Recovery of 8-oxo-dG from Porous Carbon>

Using a syringe, 1 mL of the eluent prepared above was injected into the cartridge having the porous carbon that has absorbed 8-oxo-dG so that the pressure is as constant as possible, while setting 1 mL/min as a standard, and the eluent was recovered as four 0.25 mL fractions.

The HPLC chart of the 0 mL to 0.25 mL fraction is shown in (A) of FIG. 3, the HPLC chart of the 0.25 mL to 0.5 mL fraction is shown in (B) of FIG. 3, the HPLC chart of the 0.5 mL to 0.75 mL fraction is shown in (C) of FIG. 3, and the HPLC chart of the 0.75 mL to 1.0 mL fraction is shown in (D) of FIG. 3.

As a result of calculation as a ratio % in the case where the peak area of the HPLC measurement value of the 8-oxo-dG standard solution (250 ng/mL) was set as 100, the amount of 8-oxo-dG recovered in 1 mL of the eluent was 90.9%.

The invention claimed is:

1. A method for extracting a low-molecular-weight substance existing in a biological sample from the sample, the method comprising:
   1) an adsorption step of adsorbing the low-molecular-weight substance on porous carbon by mixing the biological sample with the porous carbon having mesopores of 3.5 nm to 150 nm and micropores of a larger size as a hierarchical structure, and then recovering the porous carbon from the obtained mixture, or by bringing the biological sample into contact with a filtration filter on which the porous carbon having mesopores of 3.5 nm to 150 nm and micropores of a larger size as a hierarchical structure is disposed or supported; and
   2) a releasing step of releasing the low-molecular-weight substance from the porous carbon by mixing the porous carbon having the low-molecular-weight substance adsorbed thereon, obtained after the adsorption step, with an aqueous solution containing 0.1 mass % to 1 mass % of spherical silica having an average particle diameter of 10 nm to 100 nm and containing 10% to 12% of acetonitrile, or by causing the filtration filter obtained after the adsorption step to contact and pass through the aqueous solution.

2. The method according to claim 1, further comprising a regeneration step of regenerating the porous carbon after the releasing step for use in the adsorption step again.

3. The method according to claim 2, further comprising a pretreatment step of the biological sample before the adsorption step.

4. The method according to claim 2, wherein the spherical silica is a surface-treated spherical silica.

5. The method according to claim 4, wherein the surface-treated spherical silica has been subjected to a treatment of substituting a silanol group on the surface of the spherical silica with a phenyl group, a vinyl group, or a methacryloyloxy group.

6. The method according to claim 1, further comprising a pretreatment step of the biological sample before the adsorption step.

7. The method according to claim 6, wherein the spherical silica is a surface-treated spherical silica.

8. The method according to claim 7, wherein the surface-treated spherical silica has been subjected to a treatment of substituting a silanol group on the surface of the spherical silica with a phenyl group, a vinyl group, or a methacryloyloxy group.

9. The method according to claim 1, wherein the spherical silica is a surface-treated spherical silica.

10. The method according to claim 9, wherein the surface-treated spherical silica has been subjected to a treatment of substituting a silanol group on the surface of the spherical silica with a phenyl group, a vinyl group, or a methacryloyloxy group.

* * * * *